United States Patent
Palassis et al.

(10) Patent No.: US 10,955,341 B2
(45) Date of Patent: Mar. 23, 2021

(54) OPTICAL NITRATE SENSOR COMPENSATION ALGORITHM FOR MULTIPARAMETER WATER QUALITY MEASUREMENT

(71) Applicant: YSI, INC., Yellow Springs, OH (US)

(72) Inventors: Christopher John Palassis, Yellow Springs, OH (US); Melanie C. K. Poon, Centerville, OH (US)

(73) Assignee: YSI, INC., Yellow Springs, OH (US)

(*) Notice: Subject to any disclaimer, the term of this patent is extended or adjusted under 35 U.S.C. 154(b) by 0 days.

(21) Appl. No.: 15/454,465

(22) Filed: Mar. 9, 2017

(65) Prior Publication Data

US 2017/0299511 A1  Oct. 19, 2017

Related U.S. Application Data

(60) Provisional application No. 62/305,742, filed on Mar. 9, 2016.

(51) Int. Cl.
 *G01N 21/59* (2006.01)
 *G01J 3/42* (2006.01)
 (Continued)

(52) U.S. Cl.
 CPC .......... *G01N 21/59* (2013.01); *G01J 1/42* (2013.01); *G01J 3/10* (2013.01); *G01J 3/28* (2013.01);
 (Continued)

(58) Field of Classification Search
 None
 See application file for complete search history.

(56) References Cited

U.S. PATENT DOCUMENTS 4,248,598 A  2/1981  Blunck
4,868,127 A  9/1989  Blades et al.
(Continued)

FOREIGN PATENT DOCUMENTS

AU  657477  12/1992
CA  2589516 C  6/2006
(Continued)

OTHER PUBLICATIONS

Korostynska, O., A. Mason, and A. I. Al-Shamma'a, "Monitoring of nitrates and phosphates in wastewater: current technologies and further challenges," International journal on smart sensing and intelligent systems 5.1, Mar. 1, 2012. (pp. 149-176) http://www-ist.massey.ac.nz/s2is/issues/v5/n1/papers/paper9.pdf.
(Continued)

*Primary Examiner* — Edwin C Gunberg
(74) *Attorney, Agent, or Firm* — Ware, Fressola, Maguire & Barber LLP

(57) ABSTRACT

An optical nitrate sensor features a signal processor or signal processing module configured to:
 receive signaling containing information about a concentration of nitrate dissolved in the water based upon a first UV optical absorbance of light centered at 229 nm, and also containing information about a dissolved organic matter (DOM) sensed in the water based upon a second UV optical absorbance of associated light centered in a range of 250 nm to 275 nm; and
 determine corresponding signaling containing information about a corrected concentration of nitrate dissolved in the water by compensating the concentration of nitrate for the DOM sensed in the water, based upon the signaling received.

13 Claims, 6 Drawing Sheets

(51) Int. Cl.
*G01J 3/10* (2006.01)
*G01J 3/28* (2006.01)
*G01J 1/42* (2006.01)
*G01N 33/18* (2006.01)
*G01N 21/33* (2006.01)
*G01N 21/88* (2006.01)
*G01N 21/53* (2006.01)

(52) U.S. Cl.
CPC .............. *G01J 3/42* (2013.01); *G01N 21/33* (2013.01); *G01N 21/8806* (2013.01); *G01N 33/188* (2013.01); *G01N 21/53* (2013.01); *G01N 2201/062* (2013.01)

(56) References Cited

U.S. PATENT DOCUMENTS

| | | | |
|---|---|---|---|
| 5,244,811 | A | 9/1993 | Matthews |
| 5,420,432 | A | 5/1995 | Manook et al. |
| 5,443,991 | A | 8/1995 | Godec et al. |
| 5,630,987 | A | 5/1997 | Briggs et al. |
| 5,864,140 | A | 1/1999 | Owens |
| 6,007,777 | A | 12/1999 | Purcell et al. |
| 6,313,468 | B1 | 11/2001 | Wedekamp |
| 6,444,474 | B1 | 9/2002 | Thomas et al. |
| 6,451,613 | B1 | 9/2002 | Blades et al. |
| 6,734,021 | B1 | 5/2004 | Saito et al. |
| 6,737,276 | B1 | 5/2004 | Voss et al. |
| 7,598,086 | B2 | 10/2009 | Zhao |
| 8,557,597 | B2 | 10/2013 | Akechi et al. |
| 8,663,561 | B2 | 3/2014 | Patton |
| 8,835,875 | B2 | 9/2014 | She et al. |
| 8,957,387 | B2 | 2/2015 | Sexton et al. |
| 8,981,314 | B2 | 3/2015 | Klinkhammer et al. |
| 2004/0043499 | A1 | 3/2004 | Lee-Alvarez |
| 2004/0130397 | A1 | 7/2004 | MacTaggart |
| 2006/0091319 | A1 | 5/2006 | Steuerwald et al. |
| 2010/0283993 | A1 | 11/2010 | Preiner et al. |
| 2010/0330690 | A1 | 12/2010 | Kimoto et al. |
| 2011/0066009 | A1* | 3/2011 | Moon .................. A61B 5/0002 600/301 |
| 2016/0054228 | A1 | 2/2016 | Yahata et al. |
| 2016/0054281 | A1* | 2/2016 | Smeeton .............. G01N 21/532 250/373 |

FOREIGN PATENT DOCUMENTS

| | | |
|---|---|---|
| CN | 102042963 A | 5/2011 |
| DE | 3223167 A1 | 12/1983 |
| DE | 3324606 A1 | 1/1985 |
| DE | 19500803 A1 | 12/1995 |
| DE | 19902396 A1 | 8/2000 |
| DE | 19947940 A1 | 5/2001 |
| DE | 10228929 A1 | 1/2004 |
| DE | 102007026717 A1 | 5/2009 |
| DE | 102008028058 A1 | 12/2009 |
| EP | 0682250 A1 | 11/1995 |
| EP | 0823054 A1 | 2/1998 |
| GB | 2312278 A | 10/1997 |
| WO | 9803855 A1 | 1/1998 |
| WO | 2010051842 A1 | 5/2010 |
| WO | 2010129874 A1 | 11/2010 |

OTHER PUBLICATIONS

Cleary, John, Damien Maher, and Dermot Diamond, "Development and deployment of a microfluidic platform for water quality monitoring," Smart Sensors for Real-Time Water Quality Monitoring, Springer Berlin Heidelberg, printed on Mar. 25, 2016. (pp. 125-148) http://doras.dcu.ie/18122/1/Chapter_20130110_Development_and_deployment_of_a_microfluidic_platform.pdf.

Bridgeman, Jonathan, et al., "Portable LED fluorescence instrumentation for the rapid assessment of potable water quality," Science of the Total Environment 524, 2015. (pp. 338-346 and pp. 340-341, Figure 1) https://www.researchgate.net/profile/Andy_Baker4/publication/275366885_Portable_LED_fluorescence_instrumentation_for_the_rapid_assessment_of_potable_water_quality/links/554423590cf23ff716853b41.pdf.

Younos, Tamim, and Christopher J. Heyer, "Advances in Water Sensor Technologies and Real-Time Water Monitoring," Advances in Watershed Science and Assessment, Springer International Publishing, 2015. (pp. 171-203, see p. 115, 125-126; Figure 12; and p. 188-192).

Moore, Casey, et al., "Optical tools for ocean monitoring and research," Dec. 10, 2009.(See p. 665, Section 2.2) http://darchive.mblwhoilibrary.org/bitstream/handle/1912/3098/os-5-661-2009.pdf?sequence=1&isAllowed=y.

English language Abstract of corresponding document EP2133687 for DE102008028058.
English language Abstract for DE102007026717.
English language Abstract for DE19947940.
English language Abstract for DE19902396.
English language Abstract for DE19500803.
English language Abstract of corresponding document WO2004003524 for DE10228929.
English language Abstract of DE3324606.
English language Abstract of DE3223167.
English language Abstract of 102042963.
English language Abstract of EP0682250.

* cited by examiner

Figure 1A: The Basic Signal Processing Functionality

20

20a, Receive signaling $S_{in}$ containing information about a concentration of nitrate dissolved in the water based upon a first UV optical absorbance of light centered at 229nm, and also containing information about a dissolved organic matter (DOM) sensed in the water based upon a second UV optical absorbence of associated light centered in a range of 250nm to 275nm 20b, Determine corresponding signaling $S_{out}$ containing information about a corrected concentration of nitrate dissolved in the water by compensating the concentration of nitrate for the DOM sensed in the water, based upon the signaling received 20c, Provide corresponding signaling $S_{out}$ containing information about the corrected concentration of nitrate dissolved in the water

*FIG. 1B*: The Basic Method

FIG. 2: Flowchart 50 of at least part of a Compensation Algorithm

FIG. 3: Diagram of Corrections for nitrate measurement

FIG. 4: Graph showing the effect of a turbidity correction at a fixed 2ppm nitrate. Turbidity of 500 FNU can yield false nitrate concentration up to ~30ppm (diamonds). Implementing a correction algorithm can effectively yield accurate results (squares).

OPTICAL NITRATE SENSOR COMPENSATION ALGORITHM FOR MULTIPARAMETER WATER QUALITY MEASUREMENT

CROSS-REFERENCE TO RELATED APPLICATIONS

This application claims benefit to provisional patent application Ser. No. 62/305,742 (911-023.4-1//N-YSI-0034), filed 9 Mar. 2016, which is incorporated by reference in its entirety.

This application is also related to patent application Ser. No. 15/451,853, filed 7 Mar. 2017, which claims benefit to provisional patent application Ser. No. 62/304,678 (911-023.3-1//N-YSI-0033), filed 7 Mar. 2016, which are both incorporated by reference in their entirety.

BACKGROUND OF THE INVENTION

1. Field of Invention

This invention relates to a technique for determining the quality of water; and more particularly relates to a technique for determining the quality of water using an optical sensor for multiparameter water quality monitoring.

2. Description of Related Art

Eutrophication is understood to be an excessive richness of nutrients in a lake or other body of water, frequently due to runoff from the land, which causes a dense growth of plant life and death of animal life from lack of oxygen. Eutrophication due to such nutrient loading of such environmental water is one of the biggest challenges to aquatic health today. Nitrate detection in such environmental water is essential to help solve these problems. Current sensors available in the market are not amenable to long term monitoring due to reagent consumption (wet chemistry systems) or excessive power consumption (spectrometer-based systems). In view of this, as demand grows to reduce nutrient loading, there is a need in the art for an environmental water sensor that is part of a long-term monitoring, multiparameter sensing suite.

SUMMARY OF THE INVENTION

The Underlying Technique in General

By way of example, the present invention provides new and unique techniques for determining the quality of water using an optical sensor for multiparameter water quality monitoring, e.g., to solve the aforementioned need in the art.

According to some embodiment, the present invention provides apparatus, e.g., in the form of a multiparameter sonde-based sensor, that measures ultraviolet (UV) absorbance of nitrate at ~229 nm (nanometers) that utilizes deep UV light emitting diodes (LEDs). However, due to water matrix interferences, a single wavelength measurement is insufficient in natural water to measure nitrate concentration. Therefore, matrix correction algorithms must be employed to extract the nitrate concentration from any background interference.

Optical absorbance is a measure of light intensity attenuation, relative to a reference measurement, over a fixed distance. Nitrate dissolved in water has a well-known optical absorbance in the UV spectrum in a range from 200 nm-230 nm. Recent advances in LED technology have allowed access to the weak optical absorbance in the 229 nm range. This weak optical absorbance is sufficient to measure nitrate concentrations typical in freshwater systems of 1-10 ppm (i.e., parts per million).

To make this measurement, a UV LED, centered at 229 nm, may be configured to illuminate water confined within a prescribed region of the sensor body. Light traversing the confined volume of water is attenuated in the presence of an absorbing species. The attenuated light impinges onto a photodiode where a photocurrent is generated and is subsequently converted into a voltage via a transimpedance amplifier. This signal is designated as the measurement (M) or the measurement signal. Prior to interacting with the sample, a portion of the UV light is sampled via a reference photodiode where the photocurrent is converted into a voltage via a transimpedance amplifier without interacting with the water. This signal is designated as the reference (R) or the reference signal.

The absorbance can be calculated as follows:

$$\text{Absorbance} = -\log(\text{optical transmittance}) = -\log(M/aR),$$

where a is a proportionality constant that can be adjusted for electrical gain and/or normalization While absorbance can be measured as an attenuation as shown above, it is truly based on the concentration of an absorbing species, the interaction length with the absorbing species, and the molar absorptivity which varies with wavelength of light used. This is described by Beer's Law as Absorbance=$\varepsilon$l c; where $\varepsilon$=molar absorptivity, c=analyte concentration, and l=interaction length. This implies for optimized signal contrast, a long interaction length is needed for the lowest concentrations, and a short interaction length is needed for high concentrations.

In natural water it is imperative to correct for multiple optical interferences. The present invention proposes an implementation for using correction algorithms for or towards making a nitrate absorbance measurement.

Dissolved organic matter (DOM) such as leaves and soil extracts can optically interfere with a nitrate measurement. The interference is due to the absorbance of the incident UV light that provides the energy transfer that produces the fluorescence. This additional background absorbance can yield false positive nitrate absorbance results. To compensate for this background absorbance, a second optical source centered on the dominant DOM absorbance at 250 nm-275 nm can be implemented to measure the DOM absorbance background. This background level can then be subtracted from the nitrate measurement at 229 nm to provide a background corrected result.

Water turbidity can also interfere with a nitrate absorbance measurement. Optical scattering from particulates in the water appears as attenuation at all wavelengths of light, thus providing false absorbance. Turbidity can be measured on-board the sensor or in the system via nephelometric scattering in near infrared.

The following algorithm is typical of the compensation needed to make an accurate nitrate measurement with predominately turbidity and organic matter interferences. Temperature compensation also appears and is very important to any compensation algorithm. Correction algorithm coefficients are specific to a given sensor electrical, mechanical, and optical architecture, and are therefore, not global in nature.

1. Reference (R) and Measurement (M) photodiode signals are evaluated at 229 nm and ~275 nm. By way of example, the absorbance may be calculated via a logarithm of the ratio of the signals R and M to the ratio of a non-absorbing (blank) standard such as deionized water.

2. The turbidity correction is subtracted from the absorbance as a polynomial correction of coefficients $\alpha_i$ or $\gamma_m$, at 229 nm and ~275 nm, respectively. By way of example, turbidity data may be provided from an internal or external optical measurement in nephelometric units.

3. Turbidity compensated nitrate concentration, as milligrams/liter, can be calculated from the absorbance with a conversion factor(s) $\beta_j$.

4. Organic matter background can be corrected, e.g., via a subtraction of turbidity compensated absorbance with an appropriate scale factor, $\delta$, for the 275 nm absorbance.

5. Organic matter and turbidity corrected nitrate concentration can be calculated, e.g., via a polynomial of coefficients $\varepsilon_k$.

6. Temperature corrections of the organic background and turbidity compensated data can be calculated, e.g., via a polynomial of coefficients, $\mu(° C.)_l$.

There are multiple ways to integrate LEDs for both the measurement and correction. According to the present invention, sensors will utilize a combination source that contains 229 nm, 275 nm, and a monitor photodiode within the same optical housing. The benefit of this approach is that it minimizes the number of optical components in the system, reduces optical alignment error, and aids in the overall miniaturization of the sensor. Integrating a near IR LED for turbidity measurements in the same package is also a possibility with this approach. Each LED may be individually addressable in the circuit design so that multiple, individual measurements can made while minimizing the peak current draw of the system. Additionally, if more correction wavelengths are needed, then expanding the number of individually addressed sources or photodiodes is reasonably straightforward.

Examples of Particular Embodiments

According to some embodiments, the present invention may include apparatus, e.g., such as an optical nitrate sensor, featuring a signal processor or signal processing module configured to:

receive signaling containing information about a concentration of nitrate dissolved in the water based upon a first UV optical absorbance of light centered at 229 nm, and also containing information about a dissolved organic matter (DOM) sensed in the water based upon a second UV optical absorbance of associated light centered in a range of 250 nm to 275 nm; and determine corresponding signaling containing information about a corrected concentration of nitrate dissolved in the water by compensating the concentration of nitrate for the DOM sensed in the water, based upon the signaling received.

The apparatus may include one or more of the following additional features:

The signal processor may be configured to provide corresponding signaling containing information about the corrected concentration of nitrate dissolved in the water.

The signaling may include first signaling containing information about a first measurement (M) of the first UV optical absorbance of nitrate dissolved in water of a UV light that is generated by a UV LED centered at 229 nm and that traverses a confined volume of the water within a prescribed region of a sensor body.

The signaling may include second signaling containing information about a measurement of the second UV optical absorbance of the DOM in the water of a UV light that is generated by a UV LED centered in a range of 250 nm to 275 nm and that traverses a confined volume of the water within a prescribed region of a sensor body.

The signaling may include in combination both first signaling containing information about a first measurement (M) of the first UV optical absorbance of nitrate dissolved in water of a first UV light that is generated by a first UV LED centered at 229 nm and that traverses a confined volume of the water within a prescribed region of a sensor body, and also about a first reference sample (R) of a first portion of the first UV light not traversing the confined volume of the water; and second signaling containing information about a second measurement of the second UV optical absorbance of the DOM in the water of a second UV light that is generated by a second UV LED centered in a range of 250 nm to 275 nm and that traverses the confined volume of the water within the prescribed region of the sensor body, and also about a second reference sample (R) of a second portion of the second UV light not traversing the confined volume of the water.

The signal processor may be configured to determine background corrected signaling containing information about a background corrected concentration of nitrate dissolved in the water, based upon the second signaling received.

The signal processor may be configured to determine the background corrected signaling by subtracting the second signaling from the first signaling to compensate for leaves and soil extracts in the water that can optically interfere with a nitrate measurement.

The signal processor may be configured to:
receive further second signaling containing information about optical scattering from particulate in the water that appears as attenuation at all wavelengths of light; and turbidity corrected signaling containing information about a turbidity corrected concentration of nitrate dissolved in the water, based upon the further second signaling received.

The signal processor may be configured to receive reference (R) and measurement (M) photodiode signaling that are evaluated at 229 nm and ~275 nm, and implement a compensation algorithm having some combination of steps as follows:

determining an absorbance via a logarithm of a ratio of the reference (R) and measurement (M) photodiode signaling to a ratio of a non-absorbing or blank standard, e.g., including where the non-absorbing or blank standard is determined in relation to deionized water;

subtracting a turbidity correction from the absorbance as a polynomial correction of coefficients $\alpha_i$ or $\gamma_m$, at 229 nm and ~275 nm, respectively, e.g., including where turbidity data signaling contains information about turbidity data provided from an internal or external optical measurement in nephelometric units;

determining or calculating a turbidity compensated nitrate concentration from the absorbance, e.g., with a conversion factor(s) $\beta_j$;

correcting an organic matter background via a subtraction of a turbidity compensated absorbance with an appropriate scale factor, $\delta$, for the 275 nm absorbance;

determining or calculating an organic matter and turbidity corrected nitrate concentration, e.g., via a polynomial of coefficients $\varepsilon_k$; or/and determining or calculating temperature corrections of organic background and turbidity compensated data signaling containing information about the organic background and turbidity compensated data, e.g., via a polynomial of coefficients, $\mu(°\,C.)_l$.

The signal processor may be configured to receive reference (R) and measurement (M) photodiode signaling that are evaluated at 229 nm and ~275 nm, and implement a compensation algorithm for correcting a nitrate measurement by performing the steps, as follows:

making a temperature correction, e.g., using an internal or external temperature sensor;

making a turbidity correction, e.g. using an external or integrated turbidity measurement.

The apparatus may include, or forms part of the optical nitrate sensor.

The optical nitrate sensor may include:

a first UV LED for providing first UV light centered at 229 nm, e.g. that can traverse a confined volume of the water within a prescribed region of a sensor body; and a second UV LED for providing second UV light centered in a range of 250 nm to 275 nm, e.g., that can traverse the confined volume of the water within the prescribed region of the sensor body.

The optical nitrate sensor may include a sensor body configured to confine the volume of the water within the prescribed region.

The signal processor may be configured to determine a measurement of the UV optical absorbance based upon the following equation:

$$\text{Absorbance} = -\log(\text{optical transmittance}) = -\log(M/aR),$$

where a is a proportionality constant that can be adjusted for electrical gain normalization.

The signaling may contain information about either a measurement (M) that is measured and received from a measurement photodiode, or the reference sample (R) that is measured and received from a reference photodiode, or both, e.g., including where a photocurrent is generated and is subsequently converted into a voltage via a transimpedance amplifier.

The UV light may traverse the confined volume of the water over a varying path length that depends on a concentration range of interest for the nitrate concentration determined.

According to some embodiments, the present invention may include a method featuring steps for receiving in a signal processor or processing module signaling containing information about a concentration of nitrate dissolved in the water based upon a first UV optical absorbance of light centered at 229 nm, and also containing information about a dissolved organic matter (DOM) sensed in the water based upon a second UV optical absorbance of associated light centered in a range of 250 nm to 275 nm; and determining in the signal processor or processing module corresponding signaling containing information about a corrected concentration of nitrate dissolved in the water by compensating the concentration of nitrate for the DOM sensed in the water, based upon the signaling received.

The method may also include one or more of the features set forth above.

BRIEF DESCRIPTION OF THE DRAWING

The drawing, which are not necessarily drawn to scale, includes FIGS. 1-5, as follows.

Figure 1:
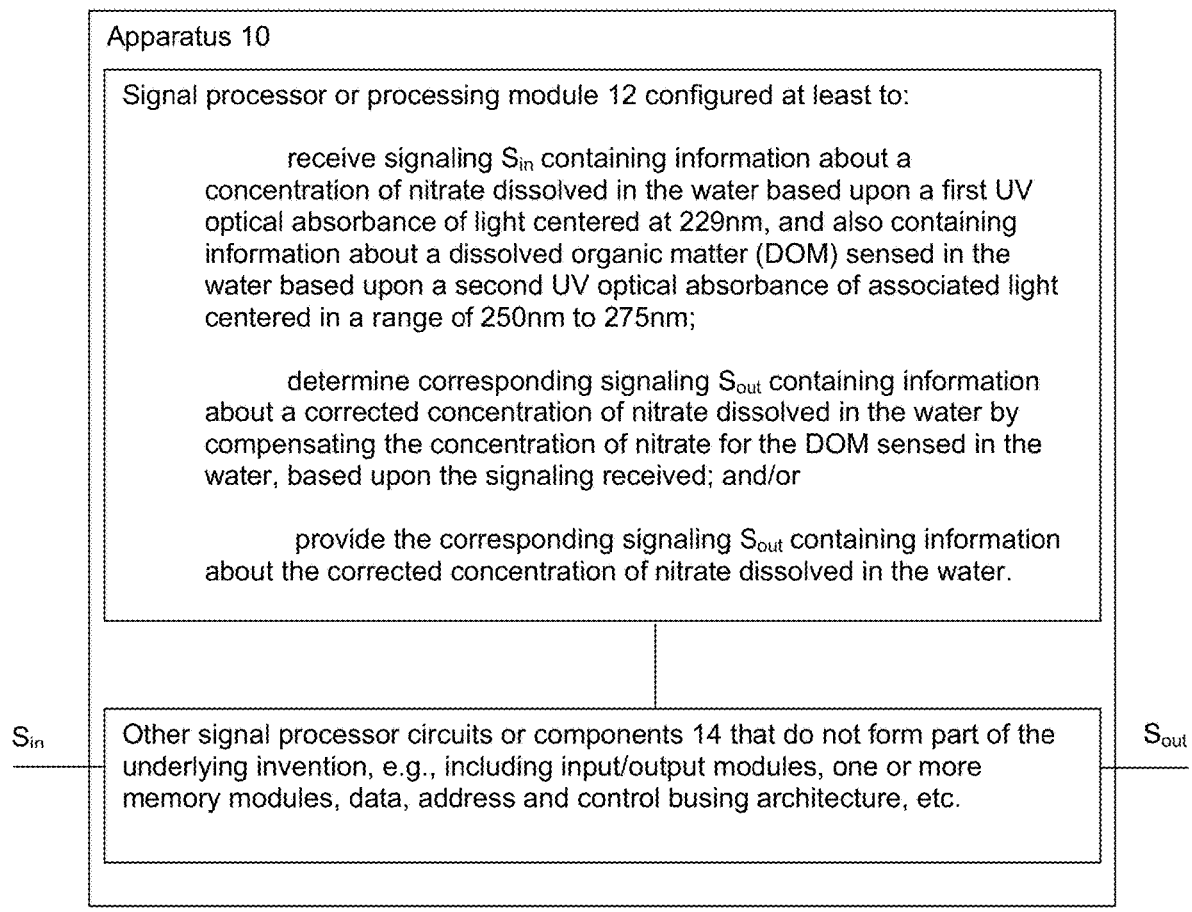
FIG. 1A shows a block diagram of apparatus, e.g., having a signal processor or signal processing module for implementing signal processing functionality, according to some embodiments of the present invention.
FIG. 1B shows a block diagram of a flowchart having steps for implementing a method, according to some embodiments of the present invention.

To reduce clutter in the drawing, each Figure in the drawing does not necessarily include every reference label for every element shown therein.

DETAILED DESCRIPTION OF BEST MODE OF THE INVENTION

FIG. 1A: Implementation of Signal Processing Functionality

By way of further example, FIG. 1A shows apparatus 10 (e.g., an optical nitrate sensor) for implementing the associated signal processing functionality, according to some embodiments of the present invention. The apparatus 10 may include a signal processor or processing module 12 configured at least to:

receive signaling containing information about a concentration of nitrate dissolved in the water based upon a first UV optical absorbance of light centered at 229 nm, and also containing information about a dissolved organic matter (DOM) sensed in the water based upon a second UV optical absorbance of associated light centered in a range of 250 nm to 275 nm; and determine corresponding signaling containing information about a corrected concentration of nitrate dissolved in the water by compensating the concentration of nitrate for the DOM sensed in the water, based upon the signaling received.

In operation, the signal processor or processing module 12 may be configured to provide the corresponding signaling containing information about the corrected concentration of nitrate dissolved in the water, e.g., for further processing, consistent with that set forth herein. The scope of the invention is not intended to be limited to any particular type, kind or manner of further processing, and may include further processing techniques either now known or later developed in the future.

By way of example, the functionality of the signal processor or processing module 12 may be implemented using hardware, software, firmware, or a combination thereof. In a typical software implementation, the signal processor or processing module 12 would include one or more microprocessor-based architectures having, e. g., at least one signal processor or microprocessor like element 12. One skilled in the art would be able to program with suitable program code such a microcontroller-based, or microprocessor-based, implementation to perform the signal processing functionality disclosed herein without undue experimentation. For example, the signal processor or processing module 12 may be configured, e.g., by one skilled in the art without undue experimentation, to receive the signaling containing information about a concentration of nitrate dissolved in the water based upon a first UV optical absorbance of light centered at 229 nm, and also containing information about a dissolved organic matter (DOM) sensed in the water based upon a second UV optical absorbance of associated light centered in a range of 250 nm to 275 nm, consistent with that disclosed herein.

Moreover, the signal processor or processing module 12 may be configured, e.g., by one skilled in the art without undue experimentation, to determine the corresponding signaling containing information about a corrected concentration of nitrate dissolved in the water by compensating the concentration of nitrate for the DOM sensed in the water, e.g., consistent with that disclosed herein. By way of example, the present application discloses techniques for determining the corresponding signaling containing information about the corrected concentration of nitrate dissolved in the water by compensating the concentration of nitrate for the DOM sensed in the water; however, the scope of the invention is not intended to be limited to any particular type or kind of signal processing implementation and/or technique for making the determination about the corrected concentration of nitrate dissolved in the water, based upon the signaling received.

The scope of the invention is not intended to be limited to any particular implementation using technology either now known or later developed in the future. The scope of the invention is intended to include implementing the functionality of the signal processor(s) 12 as stand-alone processor, signal processor, or signal processor module, as well as separate processor or processor modules, as well as some combination thereof.

By way of example, the apparatus 10 may also include, e.g., other signal processor circuits or components generally indicated 14, including random access memory or memory module (RAM) and/or read only memory (ROM), input/output devices and control, and data and address buses connecting the same, and/or at least one input processor and at least one output processor, e.g., which would be appreciate by one skilled in the art.

By way of further example, the signal processor 12 may include, or take the form of, some combination of a signal processor and at least one memory including a computer program code, where the signal processor and at least one memory are configured to cause the apparatus to implement the functionality of the present invention, e.g., to respond to signaling received and to determine the corresponding signaling, based upon the signaling received.

FIG. 1B: The Basic Method

According to some embodiments, the present invention may also include a method generally indicated as 20 comprising steps 20a, 20b and 20c, as follows:

a step 20a for receiving in a signal processor or processing module like element 12 signaling containing information about a concentration of nitrate dissolved in the water based upon a first UV optical absorbance of light centered at 229 nm, and also containing information about a dissolved organic matter (DOM) sensed in the water based upon a second UV optical absorbance of associated light centered in a range of 250 nm to 275 nm; and a step 20b for determining in the signal processor or processing module like element 12 corresponding signaling containing information about the a corrected concentration of nitrate dissolved in the water by compensating the concentration of nitrate for the DOM sensed in the water.

The method may also include one or more of the features set forth above, including a step 20c for providing the corresponding signaling containing information about the corrected concentration of nitrate dissolved in the water.

Figure 2:
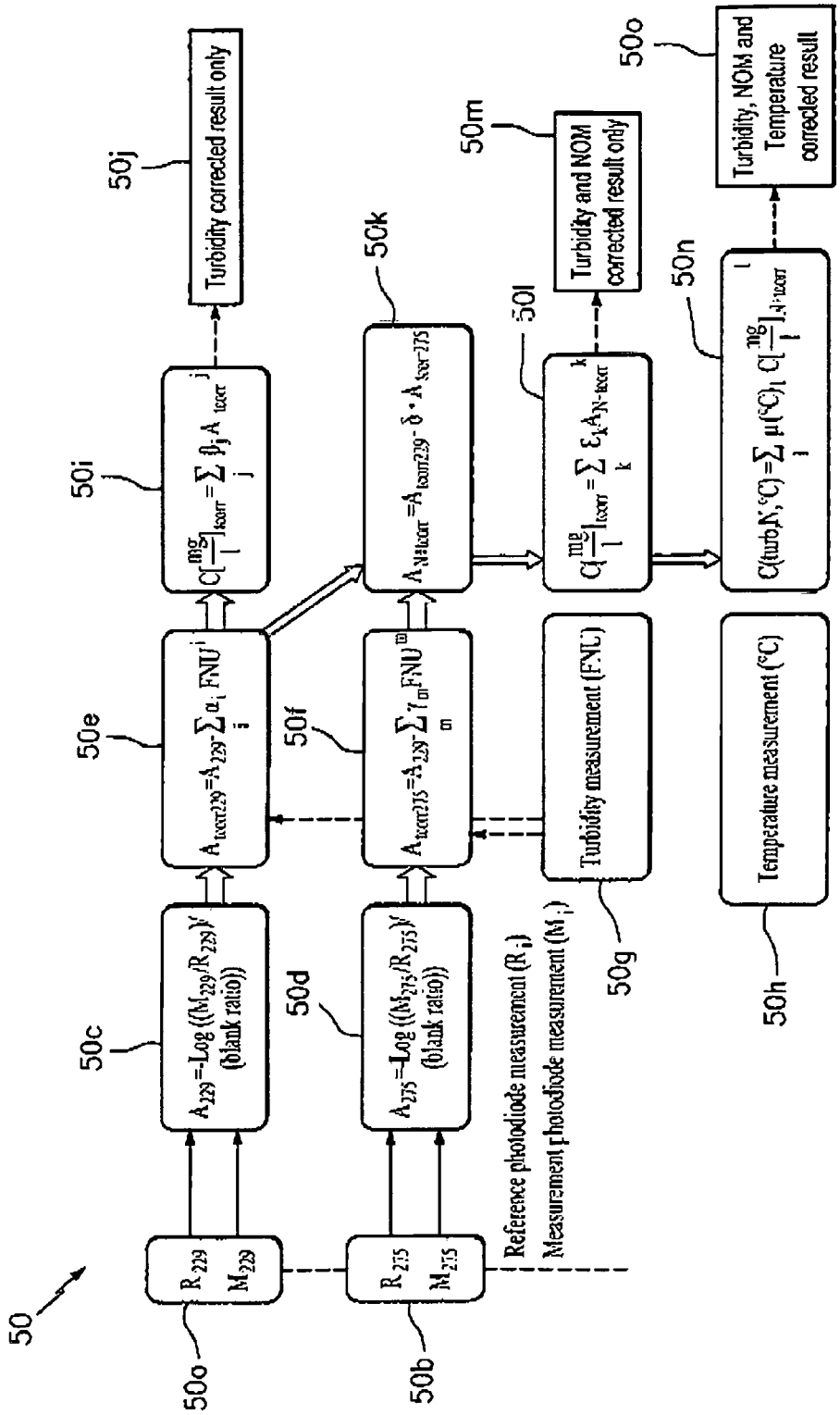
FIG. 2 is a flowchart having steps for implementing at least part of a compensation algorithm, according to some embodiments of the present invention.

FIG. 2: The Flowchart

FIG. 2 is a flowchart generally indicated as 50 having steps 50a to 50o for implementing at least part of a compensation algorithm, according to some embodiments of the present invention.

The steps are briefly summarized as follows:

Steps 50a and 50b may be implemented for determining a reference photodiode measurement and a measurement photodiode measurement;

Steps 50c and 50d may be implemented for determining $A_{229}$ and $A_{275}$, e.g., based upon determining a log function $((M_{229}/R_{229})/(blank\ ratio))$ or a corresponding log function $((M_{275}/R_{275})/(blank\ ratio))$;

Steps 50e and 50f may be implemented for determining $A_{tcorre229}$ and $A_{tcorr275}$, e.g., based upon subtracting from $A_{229}$ and $A_{275}$ a summation function related to the absorbance as a polynomial correction of coefficients $\alpha_i$ or $\gamma_m$, at 229 nm and ~275 nm, respectively;

Steps 50g and 50h may be implemented for determining a turbidity measurement and a temperature measurement;

Steps 50i, 50j and 50k may be implemented for determining a turbidity corrected results only, e.g., based upon $A_{tcorre229}$ and $A_{tcorr275}$ corrections, where the turbidity compensated nitrate concentration, as milligrams/liter, can be calculated from the absorbance with the conversion factor(s) $\beta_j$, and where the organic matter background can be corrected via the subtraction of the turbidity compensated absorbance with the appropriate scale factor, $\delta$, for the 275 nm absorbance.

Steps 50l and 50m may be implemented for determining turbidity and NOM corrected results only, e.g., based upon the organic matter and turbidity corrected nitrate concentration being calculated via a polynomial of coefficients $\varepsilon_k$; and Steps 50n and 50o may be implemented for determining turbidity, NOM and temperature corrected results only, e.g., based upon temperature corrections of the organic background and turbidity compensated data being calculated via a polynomial of coefficients, $\mu(°\ C.)$.

FIG. 3

Figure 3:
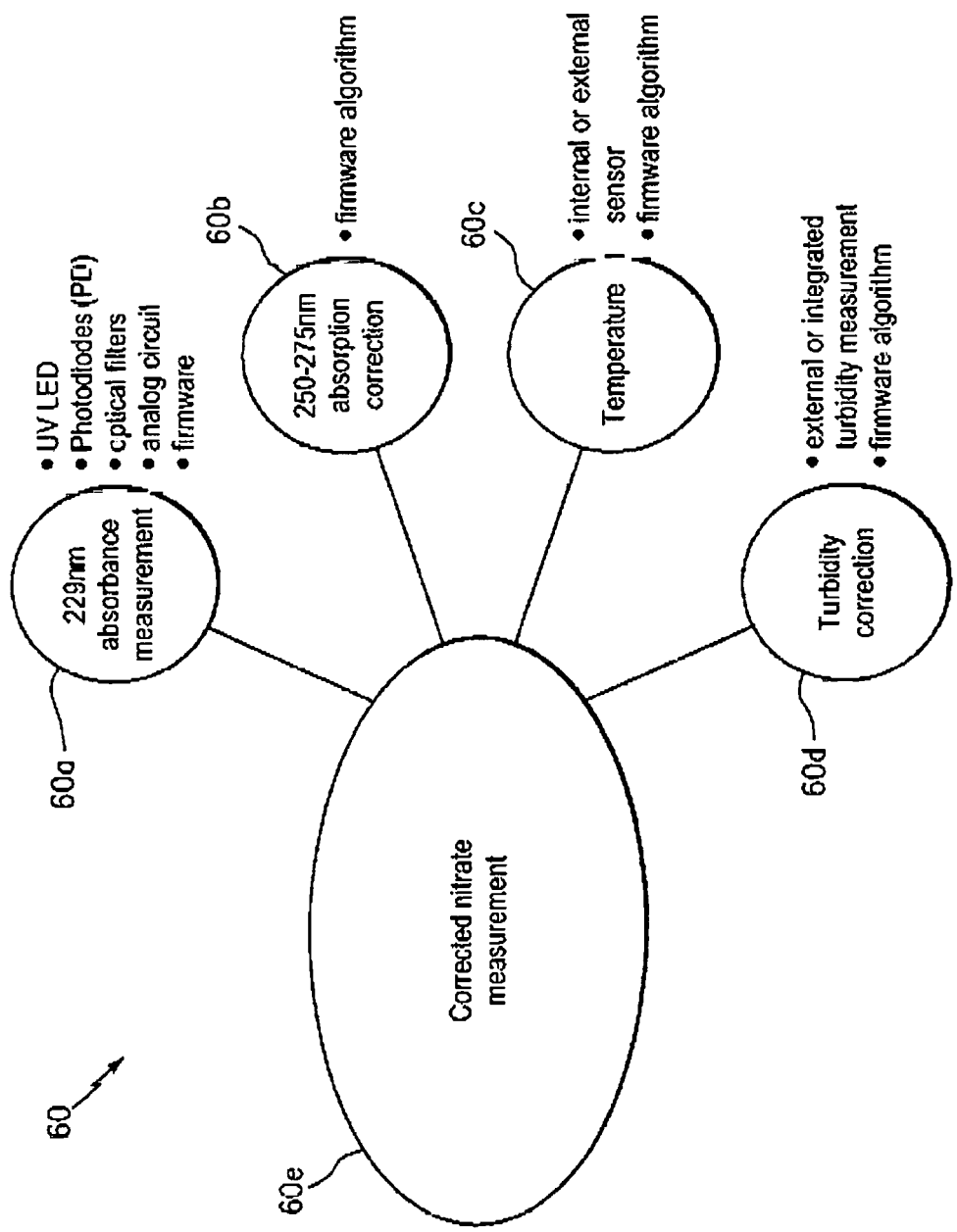
FIG. 3 is a diagram having nodes showing at least part of a compensation algorithm, according to some embodiments of the present invention.
Figure 4:
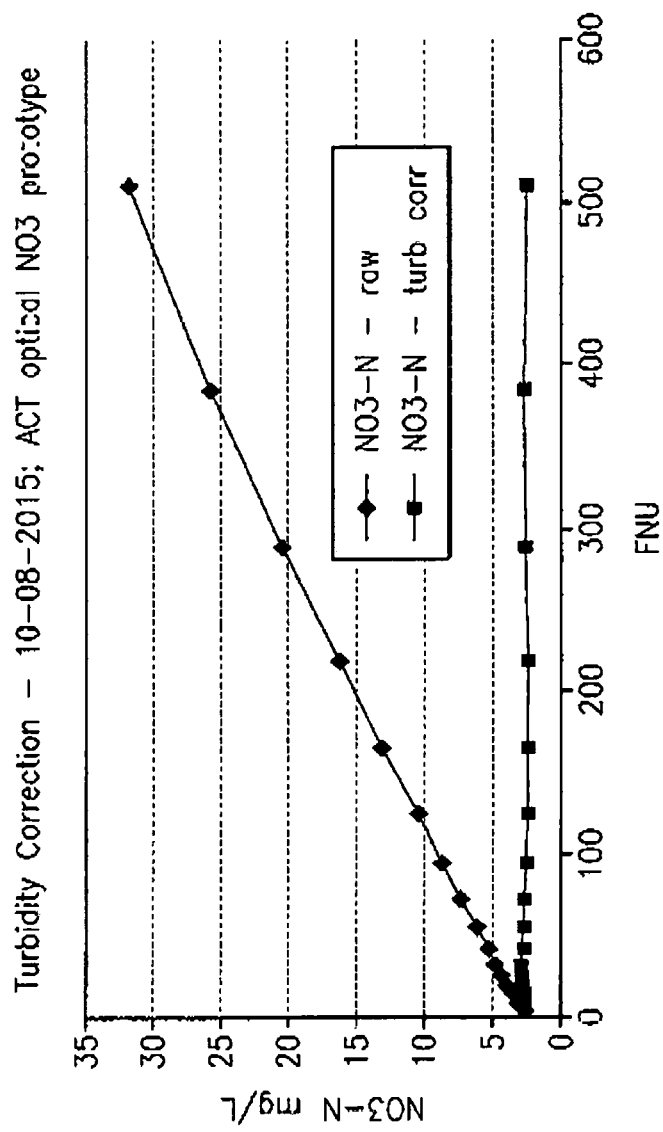
FIG. 4 is a graph showing the effect of a turbidity correction at a fixed 2 ppm nitrate, e.g., including where the turbidity of 500 FNU can yield false nitrate concentration up to ~30 ppm (diamonds), and including where implementing a correction algorithm according to the present invention can effectively yield accurate results (squares).

FIG. 3 is a diagram generally indicated as 60 having nodes 60a to 60d for implementing at least part of a compensation algorithm to obtain a corrected nitrate measurement in node 60e, according to some embodiments of the present invention.

Node 60a implements a 229 nm absorbance measurement, e.g., including by using a UV LED, photodiodes, optical filters and analog circuits and firmware, consistent with that disclosed herein;

Node 60b implements a 250 to 275 nm absorbance measurement, e.g., including by using firmware, consistent with that disclosed herein;

Node 60c implements taking a temperature measurement, e.g., using internal and external sensors and firmware algorithms, consistent with that disclosed herein; and Node 60d implements taking a turbidity measurement, e.g., using external or integrated measurements and firmware algorithms, consistent with that disclosed herein.

Figure 5:
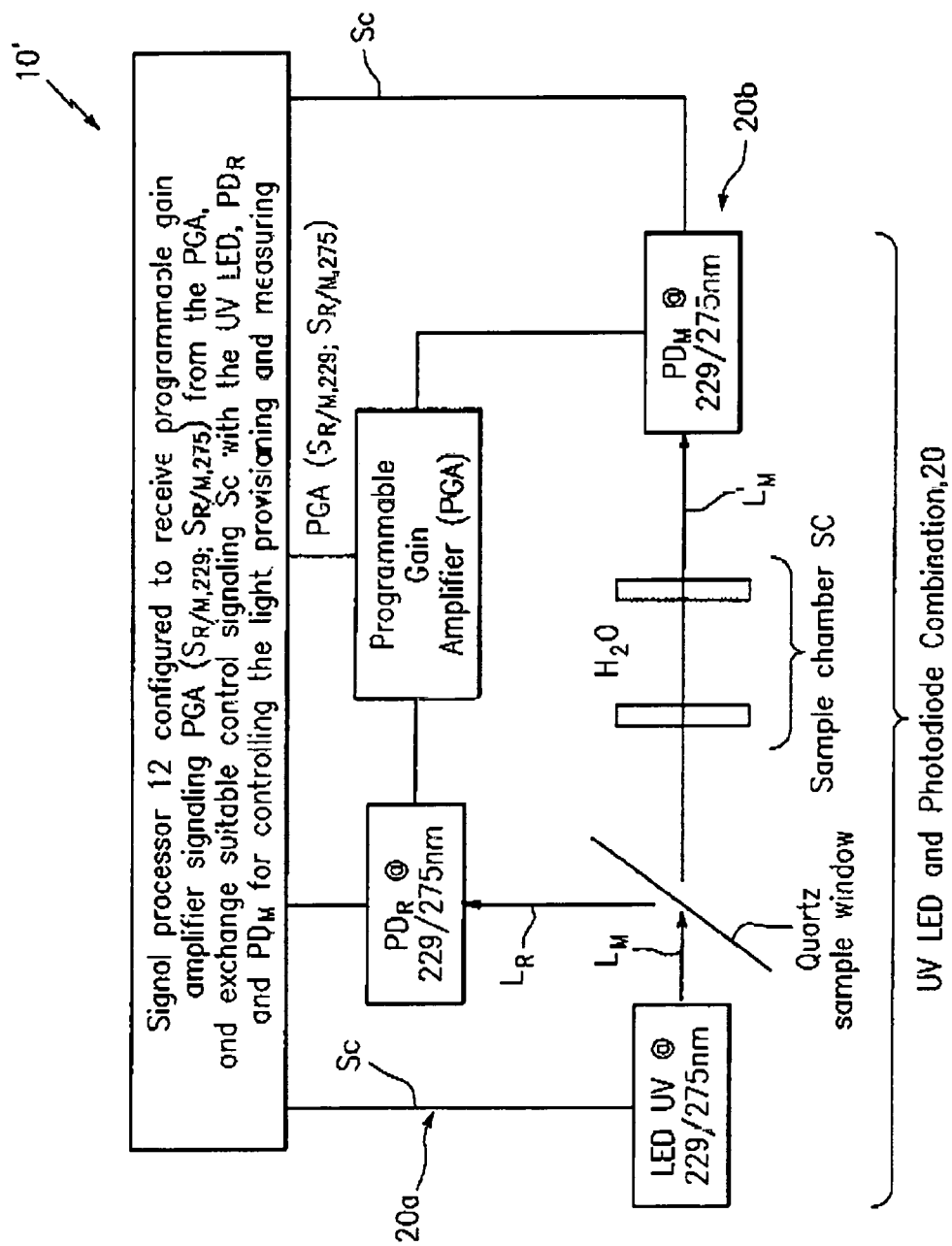
FIG. 5 shows apparatus according to the present invention, which includes a UV LED and photodiode combination for implementing the optical signaling processing functionality together with a signal processor for implementing the signaling processing functionality, all according to some embodiments of the present invention.

FIG. 5: The Basic Photodiode Combination and Signal Processing Functionality

By way of example, FIG. 5 shows apparatus generally indicated as 10' for providing optical nitrate sensor compensation for water quality monitoring of a body of water generally indicated as $H_2O$ in a sample chamber SC using a UV/LED and photodiode combination 20 and the signal processor 12.

By way of example, the UV/LED and photodiode combination 20 may include a combination source 20a having a UV LED that provides LED optical signaling $L_M$ at 229 nm or 275 nm to a sampling window, as shown that may be made of quartz. The sampling window responds to the LED optical signaling $L_M$ at 229 nm or 275 nm and provides one part of the LED optical signaling $L_M$ to a reference photodiode $PD_R$ and another part of the LED optical signaling $L_M$ at 229 nm or 275 nm through the body of water. The photodiode combination 20 also includes a monitor photodiode combination 20b having a measuring photodiode $PD_M$ that measures received LED optical signaling $L_M$ at 229 nm and 275 nm that passed through the water, and provides measured photodiode signaling $S_{m, 229}$ and $S_{m, 275}$ containing information about optical absorbsion by the water related to the LED signaling $L_M$ at 229 nm and 275 nm absorbed.

By way of further example, the UV/LED and photodiode combination 20 may also include a programmable gain amplifier PGA configured to receive the reference signaling $S_{R, 229}$ or $S_{R, 275}$ from the reference photodiodes $PD_R$, and also receive the measured signaling $S_{m, 229}$ and $S_{m, 275}$ from the measurement photodiode $PD_M$, and provide programmable gain amplifier signaling PGA ($S_{R/M, 229}$; $S_{R/M, 275}$) to the signal processor 12 for further processing, e.g., consistent with that set forth herein. Programmable gain amplifier are known in the art, and the scope of the invention is not intended to be limited to any particular type or kind thereof, e.g., either now known or later developed in the future.

The signal processor 12 is configured to receive the programmable gain amplifier signaling PGA ($S_{R/M, 229}$; $S_{R/M, 275}$), and determines output signaling $S_{out}$ containing information about the optical nitrate sensor compensation, e.g., including a turbidity correction to compensate for dissolved organic matter (DOM) contained within the water. The signal processor 12 is configured to perform signal processing functionality based upon optical nitrate sensor compensation algorithms disclosed herein to make the determination related to the optical nitrate sensor compensation to the concentration of nitrate dissolved in the water. The signal processor 12 is also configured to provide the output signaling $S_{out}$ for suitable further processing, e.g., including generating suitable display signaling for showing/displaying the information about the corrected concentration of nitrate dissolved in the water, and/or the optical nitrate sensor compensation to the concentration of nitrate, on a display/monitor, etc.

The signal processor may also be configured to provide control signaling Sc to control the operation of the UV LED, $PD_R$ and $PD_M$, e.g., to provide UV LED light at either 229 nm or 275 nm, receive/sense reference signaling at either 229 nm or 275 nm, and/or receive/sense measured signaling at either 229 nm or 275 nm, consistent with that set forth herein.

The Optical Components

By way of example, and as one skilled in the art would appreciate, optical components like LEDs, photodiodes, measurement photodiodes, reference photodiodes, optical filters, optical fiber or fibers, light pipes, LED arrays, optical sampling windows, optical pickoff windows, focusing lens, sapphire or UV grade fused silica rods, optical spectrum analyzers are all known in the art, and the scope of the invention is not intended to be limited to any particular type or kind thereof that may be used herein. The scope of the invention is intended to include using such optical components that may be now known in the art or later developed in the future.

Computer-Readable Storage Medium

According to some embodiments of the present invention, the apparatus may also take the form of a computer-readable storage medium having computer-executable components for performing the steps of the aforementioned method. The computer-readable storage medium may also include one or more of the features set forth above.

Optical Nitrate Sensor Compensation Algorithms for Multiparameter Water Quality Monitoring This application relates to the subject matter disclosed a companion patent application having Ser. No. 15/451,853, filed 7 Mar. 2017, entitled "Optical Nitrate Sensor for Multiparameter Water Quality Monitoring," which claims benefit to provisional patent application Ser. No. 62/304,678 (911-023.3-1//N-YSI-0033), filed 7 Mar. 2016. The optical nitrate sensor disclosed in the companion application may be used in conjunction with the optical nitrate sensor compensation algorithm disclosed in the instant application, and vice versa. Moreover, and by way of example, the companion patent application provides at least one technique for determining a concentration of nitrate dissolved in the water based upon a first UV optical absorbance of light centered at 229 nm, which may be compensated based upon that disclosed herein. The scope of the invention is intended to include, and embodiments are envisioned using, e.g., other techniques for determining a concentration of nitrate dissolved in the water that are both now known, and later developed in the future.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An optical nitrate sensor for sampling a confined volume of water within a prescribed region of a sampling chamber, comprising:
    a UV LED combination configured to generate a first UV LED signal centered at 229 nm and a second UV LED signal centered in a range of 250-275 nm that traverse the confined volume of water within the prescribed region of the sampling chamber in order to sense nitrates in the water with first UV LED signal and dissolved organic matter (DOM) in the water with second UV LED signal;
    a reference photodiode configured to respond to part of the first UV LED signal and the second UV LED signal, and provide photodiode reference signaling containing information about the part of the first UV LED signal and the second UV LED signal received;
    a measuring photodiode configured to sense the first UV LED signal and the second UV LED signal that pass through the confined volume of water within the prescribed region of the sampling chamber, and provide photodiode measured signaling containing information about a nitrate absorption of the water related to the first UV LED signal and a DOM absorption background related to the second UV LED signal;
    a transimpedance amplifier configured to respond to the photodiode reference signaling and the photodiode measured signaling, and provide transimpedance amplifier signaling containing information about a photocurrent to voltage reference signaling conversion of the photodiode reference signaling without interaction with the water, and also a photocurrent to voltage measured signaling conversion of the photodiode measured signaling after interaction with the water; and
    a signal processor or signal processing module configured to:
        receive the transimpedance amplifier signaling, and
        determine corresponding signaling containing information about a DOM background corrected concentration of nitrates dissolved in the water by compensating the concentration of the nitrate absorption sensed in the water at 229 nm for the DOM background absorption sensed in the water in the range of 250-275 nm, based upon the transimpedance amplifier signaling received.

2. An optical nitrate sensor, according to claim 1, where the signal processor or signal processing module is configured to provide the corresponding signaling containing information about the DOM background corrected concentration of nitrate dissolved in the water.

3. An optical nitrate sensor according to claim 1, where the UV LED is configured to respond to signaling and generate the first UV LED signal and the second UV LED signal.

4. An optical nitrate sensor, according to claim 1, wherein the signal processor or signal processing module is configured to determine the DOM background corrected concentration by subtracting the DOM background absorption from the nitrate absorption to compensate for leaves and soil extracts in the water that can optically interfere with a nitrate measurement.

5. An optical nitrate sensor, according to claim 1, wherein the signal processor or signal processing module is configured to:
    receive further signaling containing information about optical scattering from particulate in the water that appears as attenuation at all wavelengths of light; and
    determine turbidity corrected signaling containing information about a turbidity corrected concentration of nitrate dissolved in the water, based upon the further signaling received.

6. An optical nitrate sensor, according to claim 1, wherein the signal processor or signal processing module is configured to receive the photodiode reference signaling and the photodiode measured signaling, and implement a compensation algorithm for doing one or more of the following:
    determining an absorbance via a logarithm of a ratio of reference (R) and measurement (M) photodiode signaling and a ratio of a non-absorbing or blank standard, including where the non-absorbing or blank standard is determined in relation to deionized water; or
    subtracting a turbidity correction from the absorbance as a polynomial correction of coefficients $\alpha_i$ or $\gamma_m$, at 229 nm and ~275 nm, respectively, including where turbidity data signaling contains information about turbidity data provided from an internal or external optical measurement in nephelometric units; or
    determining or calculating a turbidity compensated nitrate concentration from the absorbance with a conversion factor(s) $\beta_j$; or
    correcting an organic matter background via a subtraction of a turbidity compensated absorbance with a scale factor, $\delta$, for the 275 nm absorbance; or
    determining or calculating an organic matter and turbidity corrected nitrate concentration via a polynomial of coefficients $\varepsilon_k$; or/and
    determining or calculating temperature corrections of organic background and turbidity compensated data signaling containing information about the organic background and turbidity compensated data via a polynomial of coefficients, $\mu(° C.)$.

7. An optical nitrate sensor, according to claim 1, wherein the signal processor or signal processing module is configured to receive the photodiode reference signaling and the photodiode measured signaling, and implement a compensation algorithm for correcting a nitrate measurement by doing one or more of the following:
    making a temperature correction using an internal or external temperature sensor;
    making a turbidity correction using an external or integrated turbidity measurement.

8. An optical nitrate sensor, according to claim 1, wherein the UV LED comprises:
    a first UV LED for providing first UV light centered at 229 nm and that traverses a confined volume of the water within a prescribed region of a sensor body; and
    a second UV LED for providing second UV light centered in a range of 250 nm to 275 nm.

9. An optical nitrate sensor, according to claim 1, wherein the optical nitrate sensor comprises: a sensor body configured to confine a volume of the water within the prescribed region.

10. An optical nitrate sensor, according to claim 1, wherein the signal processor or signal processing module is configured to determine a measurement of the UV optical absorbance based upon the following equation:

$$\text{Absorbance} = -\log(\text{optical transmittance}) = -\log(M/aR),$$

where a is a proportionality constant that can be adjusted for electrical gain normalization.

11. A method for sampling a confined volume of water within a prescribed region of a sampling chamber with an optical nitrate sensor, comprising:

generating with a UV LED combination a first UV LED signal centered at 229 nm and a second UV LED signal centered in a range of 250-275 nm that traverse the confined volume of water within the prescribed region of the sampling chamber in order to sense nitrates in the water with first UV LED signal and dissolved organic matter (DOM) in the water with second UV LED signal;

responding with a reference photodiode to part of the first UV LED signal and the second UV LED signal, and providing photodiode reference signaling containing information about the part of the first UV LED signal and the second UV LED signal received;

sensing with a measuring photodiode the first UV LED signal and the second UV LED signal that pass through the confined volume of water within the prescribed region of the sampling chamber, and providing photodiode measured signaling containing information about a nitrate absorption of the water related to the first UV LED signal and a DOM absorption background related to the second UV LED signal;

responding with a transimpedance amplifier to the photodiode reference signaling and the photodiode measured signaling, and providing transimpedance amplifier signaling containing information about a photocurrent to voltage reference signaling conversion of the photodiode reference signaling without interaction with the water, and also a photocurrent to voltage measured signaling conversion of the photodiode measured signaling after interaction with the water; and receiving with a signal processor or signal processing module the transimpedance amplifier signaling, and determining corresponding signaling containing information about a DOM background corrected concentration of nitrates dissolved in the water by compensating the concentration of the nitrate absorption sensed in the water at 229 nm for the DOM background absorption sensed in the water in the range of 250-275 nm, based upon the transimpedance amplifier signaling received.

12. A method according to claim 11, wherein the method comprises providing with the signal processor or signal processing module the corresponding signaling containing information about the DOM background corrected concentration of nitrate dissolved in the water.

13. A method according to claim 11, wherein the method comprises responding with the UV LED to control signaling and generating the first UV LED signal and the second UV LED signal.

* * * * *